United States Patent [19]

Van Moer et al.

[11] Patent Number: 5,232,635
[45] Date of Patent: Aug. 3, 1993

[54] CHEMILUMINESCENT SOLUTION BASED ON SUBSTITUTED ANTHRACENS

[75] Inventors: Andre Van Moer, Waterloo; Jacques Ladyjensky, Brussels, both of Belgium

[73] Assignee: American Cyanamid Company, Stamford, Conn.

[21] Appl. No.: 603,494

[22] Filed: Oct. 26, 1990

[30] Foreign Application Priority Data

Nov. 28, 1989 [BE] Belgium .............................. 08901272

[51] Int. Cl.$^5$ .................. C09K 3/00; C07C 41/00; C07C 19/08; C07C 22/00
[52] U.S. Cl. ................................... 252/700; 568/633; 568/634; 570/127; 570/183
[58] Field of Search ............. 252/700, 587, 589; 568/633, 634; 570/127, 183

[56] References Cited

U.S. PATENT DOCUMENTS

| | | | |
|---|---|---|---|
| 3,637,784 | 1/1972 | Sheehan | 252/700 |
| 3,888,786 | 6/1975 | Maulding | 252/700 |
| 4,678,608 | 7/1987 | Dugliss | 252/700 |
| 4,717,511 | 1/1988 | Koroscil | 252/700 |
| 4,751,616 | 6/1988 | Smithey | 252/700 |
| 4,859,369 | 8/1989 | Baretz et al. | 252/700 |

Primary Examiner—Robert L. Stoll
Assistant Examiner—Philip Tucker

[57] ABSTRACT

New derivatives of anthracene for the emission of a blue chemiluminescent light are disclosed. The derivatives are of 9,10-bisphenylanthracene substituted at the 2 position of the anthracene ring and on the phenyl groups. The production of turquoise chemiluminescent light is also disclosed by mixing said derivatives with a green 9,10-bis(phenylethynyl)anthracene.

8 Claims, No Drawings

CHEMILUMINESCENT SOLUTION BASED ON SUBSTITUTED ANTHRACENS

BACKGROUND OF THE INVENTION

The principle techniques for the production of chemiluminescent light have been described in great detail in U.S. Pat. No. 4,678,608 which is incorporated herein by reference.

Chemiluminescence is produced by a reaction, in the liquid phase, of an activator such as hydrogen peroxide with a fluorescent agent and an oxalate. Optionally, other secondary compounds can be present such a catalysts, dyes etc.

Until recently, there existed no simple means for the production of pure blue chemiluminescent light to the satisfaction of the user, the conventionally used fluorescent dye to obtain a blue color being 9,10-diphenylanthracene. U.S. Pat. No. 4,717,511 reveals, however, the use of a well-defined product, 9,10-bis(4-methoxyphenyl)-2-chloroanthracene, which produces a better light yield, as well as more pure blue color.

SUMMARY OF THE INVENTION

Unexpectedly, it has now been discovered that other derivatives of anthracene allow an equivalent or better yield of light emission (number of lumens-h/L) while at the same time still producing a similar, or even a more pure, blue color. Other advantages have also been often observed, for example, with regard to the ease of synthesis and purification.

In addition, it has been observed that chemiluminescent solutions prepared with fluorescers which are derivatives of 9,10-diphenylanthracenes substituted according to the present invention, when mixed with a green chemiluminescent solution based on a conventional fluorescent dye 9,10-(bis(phenylethnyl)anthracene, unexpectedly produce solutions with a turquoise color which remains stable over time, a color which was not thought to be achievable before.

DESCRIPTION OF THE INVENTION INCLUDING PREFERRED EMBODIMENTS

The new derivatives of anthracene according to the invention are prepared by a method, according to the reaction scheme given below, by aroylation of phthalic anhydride, with a 2-phenyl derivative under Friedel-Crafts reaction conditions i.e. using AlCl₃ followed by cyclization in, for example, sulfuric acid. The Grignard reagent, (R') nPhMgBR, is then added at 9,10 to the resultant anthraquinone and hydrolysis is then effected with ammonium chloride ($C_1$-$C_4$). The resultant hydrolyzed product is then reduced with potassium iodide, active acid and sodium hypophosphite under reflux conditions to form the resultant derivative which is isolated by filtering, washing with water, drying, dissolving in benzene and filtering after the addition of activated charcoal.

In the structural formulae, R represents a fluoro, chloro, bromo, alkoxy ($C_1$-$C_4$), or phenoxy subsitutent. (R')n represents one or more identical or different groups, said groups being alkoxy ($C_1$-$C_4$), phenoxy, fluoro, or polyalkylenoxy alkyl ether of 3-18 carbon atoms, n being 1-3, inclusive, except that when R is chloro, R' is not p-methoxy.

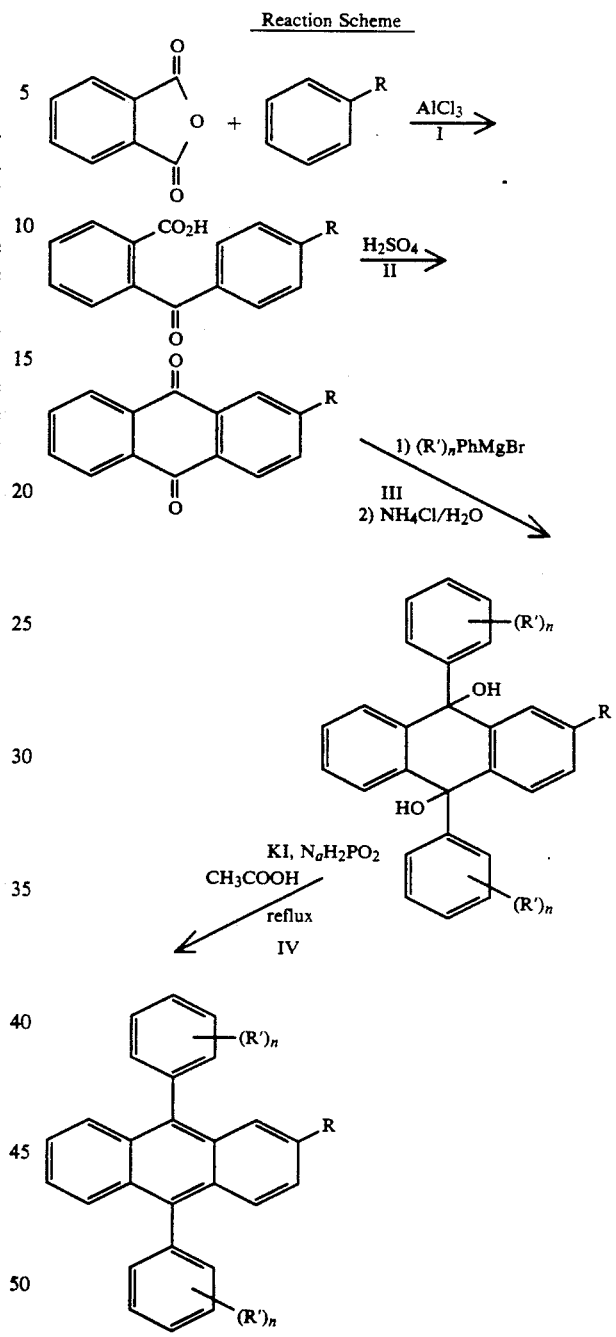

The following examples are set forth for purposes of illustration only, except as set forth in the appended claims. All parts and percentages are by weight unless otherwise specified.

EXAMPLE A (Substituted Anthraquinones)

1). M-fluorobenzene, 2) m-bromobenzene and 3) m-methoxybenzene, respectively, are added to phthalic anhydride under Freidel-Crafts reaction conditions using AlCl₃ to produce the corresponding o-aroylbenzoic acids. The acids are cyclized with sulfuric acid to yield the corresponding anthraquinones which are then recrystallized from a 2:1 benzene/ethanol mixture. 2-Chloranthraquinone is commercially available.

EXAMPLE B

(Anthracenediols)

0.2 Mol aliquots of the anthraquinones from Examples 1-3, above, are each added slowly to the Grignard Reagent (R')n-phenyl magnesium bromide, the R' being 4-ethoxy, 3,4-dimethoxy (n=2), 4-fluoro and 4-phenoxy, respectively, (said Reagents having been produced by reacting one mole of R' phenylBr and 2 mols of magnesium in 2 liters of dry tetrhydrofuran under a nitrogen atmosphere (excess magnesium being removed by filtration under nitrogen gas) and heated under reflux for 2 hours. The resultant reaction mixture is then hydrolyzed after cooling to room temperature with 200 ml of a 10% ammonium chloride solution. The tetrahydrofuran is evaporated off and the resultant residue is then extracted three items with 500 ml of hot benzene followed by drying over magnesium sulfate, filtering and evaporating again to produce the corresponding anthracenediols.

EXAMPLE C

(9,10-Bisphenylanthracenes)

100 parts of each the anthracenediols of Example B are heated with reflex in 1500 mls. of glacial acetic acid for 5 hours with 200 parts of sodium iodide and 200 parts of sodium hypophosphite. The volume of acetic acid is brought to about 500 mls and one liter of water is then added to the reaction media. The resultant mixture is then filtered and washed 3 times with 500 mls. of water. After drying, the desired product is dissolved in benzene and filtered after the addition of activated charcoal. Solvent is eliminated in a rotary evaporator and the product is recrylstallized from a 1:1 benzene/ethanol mixture. After filtration, the crystals obtained are rinsed with 200 mls of ether and dried at 50° C. for 10 hours and purified.

EXAMPLES 1-9

Utilizing the above procedures of Examples A-C, the following compounds are obtained, with the yields of anthracenediol and the final product being shown in parentheses:

EXAMPLE 1

9,10-bis(4-ethoxyphenyl)-2-chloroanthracene (87%, 80%)

EXAMPLE 2

9,10-bis(4-ethoxyphenyl)-2-fluoroanthracene (84%, 79%)

EXAMPLE 3

9,10-bis(4-ethoxyphenyl)-2-bromoanthracene (84%, 79%)

EXAMPLE 4

9,10-bis(4-ethoxyphenyl)-2-methoxyanthracene (82%, 80%)

EXAMPLE 5

9,10-bis(4-dimethoxyphenyl)-2-chloroanthracene (83%, 82%)

EXAMPLE 6

9,10-bis(3,4-dimethoxyphenyl)-2-fluroanthracene (83%, 82%)

EXAMPLE 7

9,10-bis(4-fluorophenyl)-2-chloroanthracene (80%, 78%)

EXAMPLE 8

9,10-bis(4-fluorophenyl)-2-fluoroanthracene (78%, 80%)

EXAMPLE 9

9,10-bis(4-phenoxyphenyl)-2-chloroanthracene (80%, 81%)

EXAMPLE 10

Triethyleneglycol monomethyl ether is chlorinated with thionyl chloride. The chlorinated product is then reacted with sodium p-bromophenolate to produce 4-bromo(monomethylethertriethylene glycoloxy) benzene which is then reacted with 2-chloroanthracene as per Example B, above. Example C is then followed to produce the resultant 9,10-bis[4-(monomethylethertriethyleneglycoloxyphenol)]-2-chloroanthracene (75%, 80%).

To produce chemiluminescence light, the compounds according to the present invention are used under the conditions already described in the literature, particularly in said U.S. Pat. No. 4,678,608. In general, one can use any known solvent or oxalate which can be used for the production of chemiluminescent light. The solvent can be an ester, aromatic derivatives or a chlorinated hydrocarbon. Preferably, phthalates are used, in particular dibutyl phthalate.

Oxalates, such as those described in U.S. Pat. Nos. 3,749,679 and 3,846,316, incorporated herein by reference, may be used to produce the chemical reaction to cause chemiluminescent light when mixed with the fluorescers described above, with bis(2,4,5-trichloro-6-carbopentoxylphenyl) oxalate being exemplary. Substituted carbalkoxyphenyl oxalates are the preferred class of oxalates used herein, the oxalate and fluorescer each being used in sufficient quantity to cause chemiluminescent light, preferably in a 20-40:1 oxalate to fluorescer, molar ratio.

The blue fluorescer is used in amounts ranging from about 0.005 mole per liter of oxalate solution i.e. the solvent solution of the oxalate and the fluorescer.

Useful catalysts are disclosed in U.S. Pat. No. 3,775,336, incorporated herein by reference, in concentrations disclosed therein, and usually in the solvent solution of the hydrogen peroxide.

The areas of application are well known and they include the production of useful objects, particularly signs, decorative objects, games and gadgets. In such articles, the chemiluminescent light is produced by mixing a solution of an activator, in general oxygenated water (hydrogen peroxide), with a solution which contains the novel fluorescers hereof and an oxalate diester. The article consists of, in its passive state, two compartments between which a communicating is established at the time of use, for example as described in *French Patent No.* 87 11296, for the case of flexible luminescent tubes.

EXAMPLE 11 a) Into a suitable vessel are charged 90 parts of 2,4,5-trichloro-6-carbopentoxyphenyl oxalate. The volume is increased with dibutyphthalate and heated to 150° C. under nitrogen. While stirring, there is added approximately 1 part of the fluorescer of Example 1, when the temperature reaches 90° C.

b) 50 parts of 85% hydrogen peroxide are added to an 80/20 solution of dimethylphthalate/t-butanol, to bring the volume to 1L. Next, there is added 0.180 part of sodium salicylate.

c) The solutions prepared in a) and b) are then mixed in a volume proportion of 3 to 1. The result is a chemiluminescent emission of a particularly pure blue.

EXAMPLES 12-20

Following the procedures of Example 11 except that the fluorescers of Examples 2-10 are used, similar results are obtained.

FURTHER EMBODIMENTS

In addition, it has been found that it is possible to produce compositions containing two fluorescers which are adapted to be reacted with hydrogen peroxide to provide chemiluminescent light of a color different than that emitted by either fluorescer alone. More particularly, a composition comprising a mixture of two fluorescers, each emitting a different color when used in a chemiluminescent composition, is prepared by mixing said fluorescers in amounts such as to produce a third color when the resultant composition is mixed with a peroxide. Specifically, the compounds described above and having the structure of Formula IV emit a blue light upon activation with hydrogen peroxide in chemiluminescent systems. Similarly, the known fluorescer, 9,10-bis(phenylethynyl)anthracene emits a green light under the same conditions. However, when the blue and green fluorescers are blended into a composition, the color emitted by activation with hydrogen peroxide is turquoise. Similarly, a red fluorescer can be blended with the blue fluorescer hereof to give pink. The red fluorescer of our copending U.S. application Ser. No.: 07/540,073 can be used for this purpose. This feature forms part of the scope of the invention set forth herein. The shade of the different color achieved can be attained by varying the concentration of either fluorescer. Thus, from about 95:5 to about 5:95 parts of either fluorescer can be used.

EXAMPLE 21

A solvent solution of the blue fluorescer of Example 1 is mixed with 1,6,7,12-tetraphenoxy-N,N'-bis(2,6-diisopropyl-phenyl)-3,4,9, 10-perylene dicarboximide in an amount of 91:9, respectively. A pink color is observed upon activation of the solvent mixture with a hydrogen peroxide solution.

EXAMPLE 22

The procedure of Example 21 is again followed except that the two fluorescers are that of Example 8 and 9,10-bis(phenylethynyl)anthracene and the ratio of fluorescers is 73:27. The color emitted is turquoise.

We claim:

1. A compound selected from the group consisting of 9,10-bis(fluorophenyl)-2-fluoroanthracene and 9,10-bis(phenoxyphenyl)-2-chloranthracene.

2. A composition adapted to be reacted with hydrogen peroxide to provide chemiluminescent light, said composition containing a compound of claim 1.

3. A composition according to claim 2 comprising, in addition thereto, a solvent for said compound.

4. A composition according to claim 2 comprising, in addition thereto, an oxalate compound.

5. A composition according to claim 4 wherein said oxalate is a substituted carbalkoxyphenyl oxalate.

6. A composition according to claim 5 wherein said oxalate is bis(2,4,5-trichloro-6-carbopentoxyphenyl) oxalate.

7. A composition according to claim 3 wherein said solvent is dibutylphthalate.

8. A method of producing chemiluminescent light which comprises adding to the composition of claim 4, a solution of hydrogen peroxide.

* * * * *

UNITED STATES PATENT AND TRADEMARK OFFICE
CERTIFICATE OF CORRECTION

PATENT NO. : 5,232,635
DATED : August 3, 1993
INVENTOR(S) : Van Moer et al.

It is certified that error appears in the above-indentified patent and that said Letters Patent is hereby corrected as shown below:

On the Title Page, item [54] and column 1, line 3, change "ANTHRACENS" to --ANTHRACENE--.

Signed and Sealed this

Twenty-first Day of March, 1995

Attest:

BRUCE LEHMAN

Attesting Officer     Commissioner of Patents and Trademarks